United States Patent [19]

Schwander

[11] Patent Number: 4,801,406
[45] Date of Patent: Jan. 31, 1989

[54] DICYANOBENZANTHRONE COMPOUNDS

[75] Inventor: Hansrudolf Schwander, Riehen, Switzerland

[73] Assignee: Ciba-Geigy Corporation, Ardsley, N.Y.

[21] Appl. No.: 23,593

[22] Filed: Mar. 9, 1987

[30] Foreign Application Priority Data

Mar. 18, 1986 [CH] Switzerland ............... 1088/86

[51] Int. Cl.$^4$ ............................................. C07C 50/22
[52] U.S. Cl. ........................................................ 260/352
[58] Field of Search ............... 260/352, 369; 558/374, 558/405, 445, 370, 375

[56] References Cited

U.S. PATENT DOCUMENTS 2,117,720  5/1938  Hopff et al. .................. 260/352
4,175,193  1/1974  Kadin ........................... 558/405

OTHER PUBLICATIONS

Abrahart, *Dyes and Their Intermediates*, 1968, p. 8.

*Primary Examiner*—Glennon H. Hollrah
*Assistant Examiner*—Raymond Covington
*Attorney, Agent, or Firm*—Kevin T. Mansfield; Edwards McC. Roberts

[57] ABSTRACT

The dyes of formula (1) as indicated in claim 1 are obtained by reacting 1-aminoanthraquinones with malodinitrile in the presence of titanium tetrachloride and a tertiary amine. These dyes are suitable e.g. for dyeing polyester material.

14 Claims, No Drawings

DICYANOBENZANTHRONE COMPOUNDS

The present invention relates to novel dicyanobenzanthrone compounds, to their preparation, and to the use thereof for dyeing and printing semi-synthetic or synthetic hydrophobic material.

The novel dicyanobenzanthrone compounds have the formula

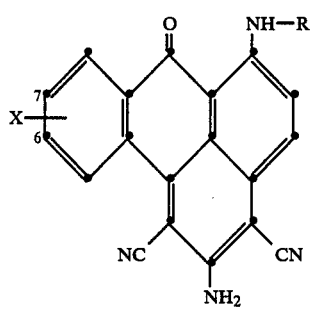

wherein

R is hydrogen or an unsubstituted or substituted alkyl or aryl radical, and

X is hydrogen or halogen which is in 6- or 7-position.

An alkyl group R is an unsubstituted or substituted, unbranched or branched alkyl radical or a cycloalkyl radical. The cycloalkyl radical preferably has 5 to 8 carbon atoms, whereas the open chain alkyl radical has preferably 1 to 8 carbon atoms.

Examples of suitable unbranched or branched open chain alkyl radicals are: methyl, ethyl, n-propyl, isopropyl, n-butyl, sec-butyl or tert-butyl, n-pentyl and isopentyl, n-hexyl and isohexyl or 2-ethyl-n-hexyl.

These alkyl radicals can carry one or more substituents, e.g. OH, $C_1$-$C_4$alkoxy, $C_1$-$C_4$alkoxy which is substituted by OH, or phenyl, phenoxy or phenylcarbamoyl, the phenyl moiety in each of which last three mentioned radicals may be substituted e.g. by $C_1$-$C_4$alkyl, $C_1$-$C_4$alkoxy, sulfo or phenoxy. Examples of suitable radicals of this kind are: hydroxyethyl, 1-hydroxyisopropyl, ethoxymethyl, 2-hydroxyethoxypentyl, benzyl, 1-phenylethyl, 2-phenylethyl, 1-methyl-2-phenylethyl, 1-isobutyl-3-phenylpropyl, 1,5-diphenylpent-3-yl, 1-methyl-2-phenoxyethyl or 1-methyl-2-phenylcarbamoyl-ethyl.

R as an unsubstituted or substituted $C_5$-$C_8$cycloalkyl radical is preferably cyclopentyl or cyclohexyl. Suitable substituents of these radicals are preferably $C_1$-$C_4$alkyl groups, most preferably the $CH_3$ group.

R as an aryl group is preferably a naphthyl radical and, most preferably, a phenyl radical. These radicals may be substituted, e.g. by $C_1$-$C_4$alkyl, $C_1$-$C_4$alkoxy, sulfo, halogen such as fluorine, chlorine or bromine, nitro, $C_1$-$C_4$alkylcarbonylamino or $C_1$-$C_4$alkoxycarbonyl.

In preferred dyes of formula I, R is $C_1$-$C_6$alkyl which is unsubstituted or substituted by phenyl, phenoxy or phenylcarbamoyl, the phenyl moiety in each of which last three mentioned radicals may be substituted by $C_1$-$C_4$alkyl, $C_1$-$C_4$alkoxy or phenoxy, or is phenyl or phenyl which is substituted by $C_1$-$C_4$alkyl.

In the dyes of formula (1), X is halogen such as bromine or, preferably, chlorine, which is in 6- or 7-position, or is preferably hydrogen.

The novel dicyanobenzanthrone compounds of formula (1) are obtained e.g. by reacting an aminoanthraquinone of formula

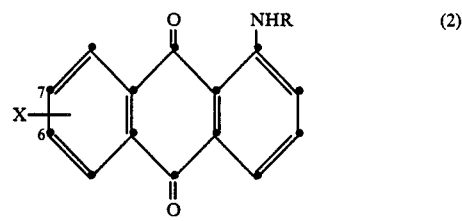

wherein X and R are as defined for formula (1), with malodinitrile in an inert solvent and in the presence of titanium tetrachloride and a tertiary amine.

Examples of suitable inert solvents are aliphatic hydrocarbons such as n-pentane, n-hexane or n-heptane; chlorinated hydrocarbons such as methylene chloride, chloroform or tetrachloromethane; ethers such as diethyl ether; or aromatic compounds such as nitrobenzene or halobenzenes. It is preferred to use a chlorinated hydrocarbon, especially methylene chloride.

The tertiary amine employed is e.g. an aliphatic amine such as triethylamine or, preferably, an aromatic amine such as picoline or pyridine.

At least 2 moles, preferably 2.2 to 3 moles, of malodinitrile are used per mole of anthraquinone compound of formula (2). While a greater excess of malodinitrile in general is not harmful, it is inexpedient.

The amount of titanium tetrachloride is preferably 2 to 10 moles, most preferably 3 to 6 moles, per mole of the anthraquinone compound of formula (2).

The tertiary amine is employed in an amount which is at least sufficient to bind the acid that is formed. Normally, however, an excess of amine will be used, preferably 2 to 6 moles per mole of titanium tetrachloride.

The reaction temperature is normally in the range from $-10°$ to $+60°$ C., preferably from $0°$ to $+25°$ C.

It must be regarded as surprising that, in the reaction of the anthraquinone compound of formula (2) with malodinitrile, a dicyanobenzanthrone is formed.

The compounds of formula (1) can be used as dyes for dyeing and printing semi-synthetic and, in particular, synthetic hydrophobic fibre materials, especially textile materials. Textile materials made from fibre blends that contain such semi-synthetic or synthetic hydrophobic textile materials can also be dyed or printed with the dyes of this invention.

Suitable semi-synthetic textile materials are in particular cellulose 2½-acetate and cellulose triacetate.

Synthetic hydrophobic textile materials consist in particular of linear polyesters, for example condensates of terephthalic acid and glycols, especially ethylene glycol, or condensates of terephthalic acid and 1,4-bis(hydroxymethyl)hexahydrobenzene; or of polycarbonates, e.g. those obtained from α,α-dimethyl-4,4'-dihydroxydiphenylmethane and phosgene; or of polyvinyl chloride or polyamide fibres.

Application of the compounds of this invention to the textile materials is made by known dyeing processes. For example, polyester fabrics are dyed by the exhaust process from an aqueous dispersion in the presence of conventional anionic or nonionic dispersants and, if appropriate, of conventional swelling agents (carriers) in the temperature range from 80° to 140° C. It is preferred to dye cellulose 2½ acetate in the temperature range from about 65° to 85° C., and cellulose triacetate in the range up to 115° C.

In the dyebath the novel dyes simultaneously dye any wool and cotton component present either not at all or only to an insignificant degree (very good reservation), so that they can also be readily used for dyeing the polyester component of polyester/wool and polyester/cellulose blends.

The dyes of this invention are especially suitable for dyeing by the thermosol process and for textile printing.

The textile material can be in any form of presentation, e.g. as fibres, filaments or webs, as woven or knitted goods.

Prior to their use, it is convenient to convert the dyes into a dyestuff formulation. This is achieved by grinding the dye such that it has an average particle size of 0.01 to 10 μm. Grinding can be effected in the presence of a dispersant. For example, the dried dye is ground with a dispersant, or kneaded in paste form with a dispersant, and then dried under vacuum or by atomising. The dyestuff formulations so obtained can be used for dyeing and printing after addition of water.

Conventional thickeners are used for printing, e.g. modified or unmodified natural products such as alginates, British gum, gum arabic, crystal gum, locust bean flour, tragacanth, carboxymethyl cellulose, hydroxyethyl cellulose, starch or synthetic products, e.g. polyacrylamides, polyacrylic acid or copolymers thereof, or polyvinyl alcohols.

The dyes of the present invention are substantially nonsensitive to carriers and impart to the cited materials, especially polyester material, level bluish red to violet shades of very good general use fastness properties, in particular good lightfastness, good fastness to sublimation, heat setting, pleating, chlorine and good wetfastness properties such as fastness to water, perspiration and washing.

The dyeings are further characterised by good pH stability and very good crockfastness. In addition, dyeings of high tinctorial strength are obtained which exhibit no catalytic fading.

The dyes of this invention can also be readily used for obtaining combination shades together with other dyes. It is, of course, also possible to use mixtures of dyes of this invention with one another.

The novel dyes are also suitable for colouring and pigmenting high molecular organic materials, e.g. cellulose ethers and esters such as ethyl cellulose, nitrocellulose, cellulose acetate, cellulose butyrate natural resins or synthetic resins such as polymerisation resins or condensation resins, for example aminoplasts, in particular urea/formaldehyde and melamine/formaldehyde resins, alkyd resins, phenolic plastics, polycarbonates, polyolefins such as polystyrene, polyvinyl chloride, polyethylene, polypropylene, polyacrylonitrile, polyacrylates, polyamides, polyurethanes or polyesters, rubber, casein, silicone and silicone resins, singly or in mixtures.

It is immaterial whether the above high molecular compounds are in the form of plastics, melts or of spinning solutions, varnishes, paints or printing inks. Depending on the end use, it is advantageous to use the compositions as toners or in the form of preparations.

The dyes can be used in the form in which they are obtained in the synthesis. In lightly ground form they afford opaque colourations. However, they can subjected to more thorough grinding, in which case they give transparent colourations, for example tinctorially strong metal effect finishes.

Thermoplastics which can be coloured in the melt with the novel dyes of formula (1) are polystyrene and the copolymers thereof, polycarbonates, polyamides and, in particular, linear polyesters.

Suitable linear polyesters are in particular those which are obtained by the polycondensation of terephthalic acid or esters thereof with glycols of the formula HO—$(CH_2)_n$—OH, in which n is an integer from 2 to 10, or with 1,4-di(hydroxymethyl)cyclohexane, or by the polycondensation of glycol ethers of hydroxybenzoic acids, for example p-(β-hydroxyethoxy)-benzoic acid. The term "linear polyesters" also comprises copolyesters which are obtained by partial replacement of terephthalic acid by another dicarboxylic acid or by a hydroxycarboxylic acid and/or by partial replacement of the glycol by another diol. The preferred linear polyesters, however, are polyethylene terephthalates.

The linear polyesters to be coloured are intimately mixed with the dye, conveniently in the form of powders, chips or granulates. This can be effected e.g. by sprinkling the polyester particles with the finely divided dry dye powder or by treating the polyester particles with a solution or suspension of the dye in an organic solvent and subsequently removing the solvent.

Finally, the colorant can also be added direct to the melt of the polyester or also before or during the polycondensation of the polyethylene terephthalate.

Depending on the desired tinctorial strength, the ratio of dye to polyester can vary within wide limits. In general, it is expedient to use 0.01 to 2 parts of dye per 100 parts of polyester.

The so treated polyester particles are fused by known methods in an extruder and pressed to objects, especially sheets or fibres, or cast to boards.

The objects obtained are coloured in level and strong bluish red to violet shades of excellent fastness to light and migration. The fibres obtained according to this invention have in addition outstanding fastness to wet and dry cleaning.

A particular advantage of the dyes of this invention is that they dissolve in the melt of the polyester and withstand high temperatures up to 300° C. without decomposing, so that substantially clearer colourations are obtained than when using insoluble pigments.

Further objects of the present invention are the above mentioned use of the benzanthrone compounds of formula (1) and a process for dyeing or printing semi-synthetic fibre or synthetic fibre material, especially textile material, which process comprises applying one or more compounds of formula (1) to said material or incorporating them therein. The cited hydrophobic fibre material is preferably textile polyester material. Further substrates which can be treated by the process of the invention, as well as preferred process conditions, will be found in the above more detailed discussion of the compounds of the invention.

The invention also relates to the hydrophobic fibre material, preferably polyester textile material, dyed or printed by the described process.

The following Examples describe the invention in more detail, but within implying any limitation to what is described therein. Unless otherwise indicated, parts and percentages are by weight.

Example 1: With efficient stirring, a mixture of 14.2 g of the compound of formula

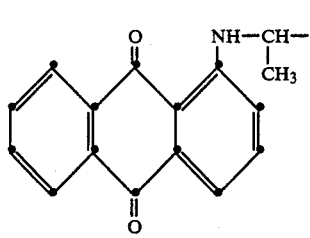

7 g of malodinitrile and 250 ml of methylene chloride is treated dropwise at 0°–5° C. over 30 minutes with 23 ml of titanium tetrachloride and then, at the same temperature, over 30 minutes with 70 ml of pyridine. The mixture is stirred for 2 hours, during which time the temperature rises to 20° C. The volatile constituents are then removed under vacuum in a rotary evaporator and the residue is treated with 200 ml of 2N HCl. After filtration and washing with 2N HCl, the filter cake is washed with water until the washings are neutral and then with methanol to remove brown by-products. After intermediate drying, the product is recrystallised from 10 parts of ethyl cellosolve, affording the dye as a dark violet powder in a yield of 80%. Melting point: 196° C.

The dye has the formula

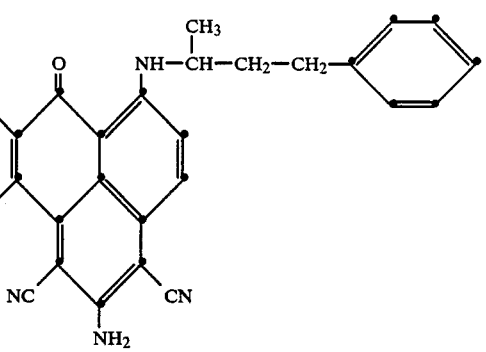

which is in accord with the elemental analysis, the mass spectrum, the proton resonance spectrum and the $^{13}$C-nuclear resonance spectrum.

When applied as disperse dye by conventional methods to polyester, brilliant bluish red shades of good fastness properties, especially good fastness to sublimation and light, are obtained.

Examples 2–9: The same procedure, but using appropriate 1-alkylaminoanthraquinones and arylaminoanthraquinones, gives the dyes listed in the following table which have similar properties and dye polyester in the indicated shade.

TABLE

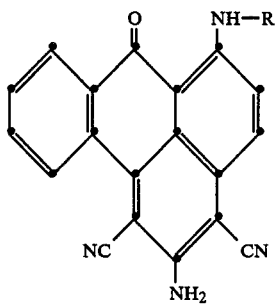

| Example | R | Shade on polyester fibres |
|---|---|---|
| 1 | —CH$_3$ | bluish red |
| 3 | —C$_2$H$_5$ | bluish red |
| 4 | —CH$_2$—CH$_2$—CH$_3$ | bluish red |
| 5 | —CH(CH$_3$)$_2$ | bluish red |
| 6 | —CH$_2$—CH$_2$—CH$_2$—CH$_3$ | bluish red |
| 7 | —CH(CH$_3$)(C$_2$H$_5$) | bluish red |
| 8 | —CH$_2$—CH(C$_2$H$_5$)—CH$_2$—CH$_2$—CH$_2$—CH$_3$ | |
| 9 | —C$_6$H$_5$ | bluish red |

TABLE-continued
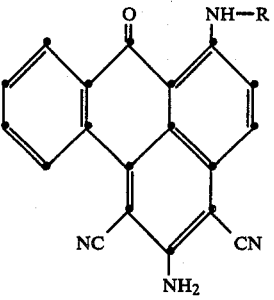
| Example | R | Shade on polyester fibres |
|---|---|---|
| 10 | 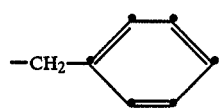 —CH$_2$— | bluish red |
| 11 | 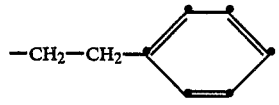 —CH$_2$—CH$_2$— | bluish red |
| 12 | 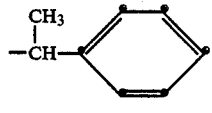 CH$_3$ / —CH— | bluish red |
| 13 | 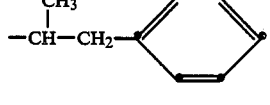 CH$_3$ / —CH—CH$_2$— | bluish red |
| 14 | 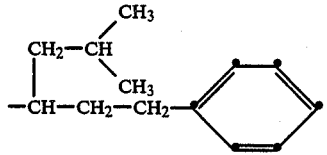 CH$_3$ / CH$_2$—CH \ CH$_3$ —CH—CH$_2$—CH$_2$— | bluish red |
| 15 | 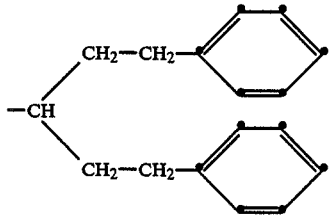 CH$_2$—CH$_2$— —CH \ CH$_2$—CH$_2$— | bluish red |
| 16 | CH$_3$ ... —CH$_3$ | reddish violet |
| 17 | 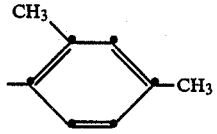 CH$_3$ ... CH$_3$ | reddish violet |

TABLE-continued
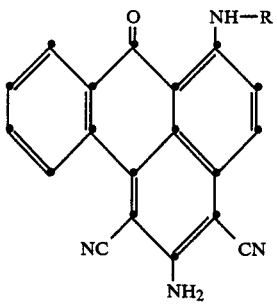
| Example | R | Shade on polyester fibres |
|---|---|---|
| 18 | 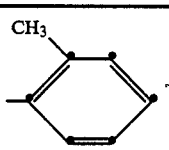 | reddish violet |
| 19 | 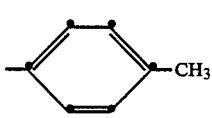 | reddish violet |
| 20 | 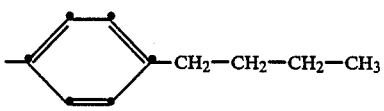 | reddish violet |
| 21 | 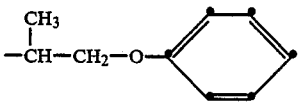 | bluish red |
| 22 | 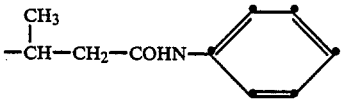 | bluish red |
| 23 | 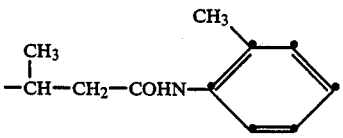 | bluish red |
| 24 | 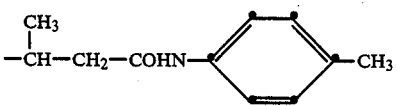 | bluish red |
| 25 | 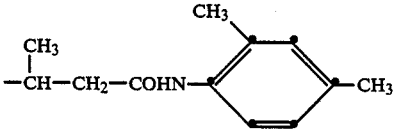 | bluish red |
| 26 | 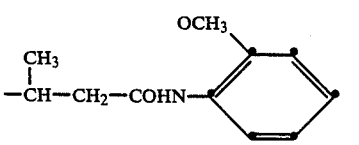 | bluish red |

TABLE-continued

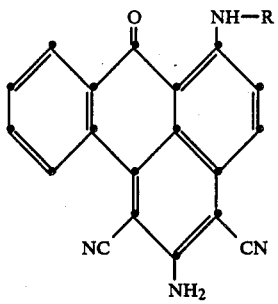

| Example | R | Shade on polyester fibres |
|---|---|---|
| 27 | —CH(CH₃)—CH₂—COHN—C₆H₄—OCH₃ | bluish red |
| 28 | —CH(CH₃)—CH₂—COHN—C₆H₄—O—C₆H₅ | bluish red |
| 29 | —CH(CH₃)—CH₂—COHN—C₆H₄—O—C₆H₅ | bluish red |

Example 30: 4 g of the product obtained in Example 1 is added to 20 ml of sulfuric acid monohydrate and the mixture is stirred for 18 hours at a temperature in the range from 20°–25° C. and then poured on to ice. The precipitate is isolated by filtration and washed with 10% sodium chloride solution. The filter cake is then suspended in 200 ml of water. The pH of the suspension is adjusted to 7 with sodium hydroxide solution, the mixture is heated to 70° C. and then 20 g of sodium chloride are added. The precipitate is isolated warm by filtration, washed with a small amount of 10% sodium chloride solution, and subsequently vacuum dried at 60° C., to give the sodium salt of the dye of the formula

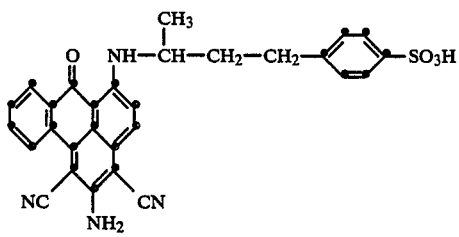

in the form of a violet powder that dissolves in water to form a violet solution.

Polyamide can be dyed in reddish violet shades with this dye from a weakly acid solution.

Example 31: The procedure of Example 1 is repeated, except that 14.2 g of 1-phenylisobutylaminoanthraquinone are replaced by an equivalent amount of 6-chloro-1-phenylisobutylaminoanthraquinone. The resultant dye of formula

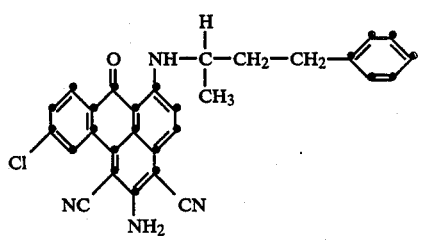

dyes polyester in bluish red shades of good fastness properties.

Example 32: 1 part of the dry, non-reduced dye obtained in Example 1 is mixed in a glass bead mill with 1 part of dinaphthylmethanedisulfonate (Na salt) and water and the mixture is ground until the particle size is about 2μ or smaller. The resultant paste, consisting of dye, dispersant and water, is thereafter mixed with 3 parts of sodium lignosulfonate. The paste is then spray dried to give a powdered formulation.

This dye formulation can be used for dyeing polyester materials, e.g. by the HT process, and imparts to the dyebath a good dispersion stability. A bluish red dyeing of good light fastness is obtained on the polyester.

Example 33: 2 parts of the dye obtained in Example 1 are dispersed in 4 000 parts of water. To this dispersion are added 12 parts of the sodium salt of o-phenylphenol and 12 parts of diammonium phosphate. 100 parts of polyethylene glycol terephthalate yarn are dyed in this liquor for 90 minutes at 95°-98° C. The dyeing is subsequently rinsed and subjected to an aftertreatment with aqueous sodium hydroxide and a dispersant to give a brilliant bluish red dyeing which is fast to light and sublimation.

Example 34: 1 part of the dye obtained in Example 1 is ground wet with 2 parts of a 50% aqueous solution of the sodium salt of dinaphthylmethanedisulfonic acid and dried. The dye formulation so obtained is stirred in 40 parts of a 10% aqueous solution of N-benzylheptadecylbenzimidazoledisulfonic acid and 4 parts of a 40% solution of acetic acid. A dyebath of 4 000 parts is prepared therefrom by dilution with water.

100 parts of polyester fabric is put into this bath at 50° C., the temperature is raised to 120°-130° C. over ½ hour, and dyeing is performed for 1 hour at this temperature in a closed vessel. The goods are subsequently thoroughly rinsed. A brilliant bluish red dyeing of good lightfastness is obtained.

Example 35: Polyethylene glycol terephthalate fabric is impregnated on a pad at 40° C. with a liquor of the following composition:
20 parts of the dye obtained in Example 1, finely dispersed in
10 parts of sodium alginate,
20 parts of triethanolamine,
20 parts of octylphenol polyglycol ether, and
930 parts of water.

The fabric is pinched off to a pick-up of about 100%, dried at 100° C., and fixed for 30 seconds at a temperature of 210° C. The dyed goods are rinsed with water, soaped and dried, to give a brilliant, lightfast, bluish red dyeing.

What is claimed is:

1. A compound of the formula

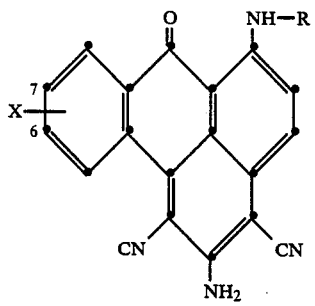

wherein
R is hydrogen or $C_1$-$C_8$alkyl which is unsubstituted or substituted by OH, $C_1$-$C_4$alkoxy or $C_1$-$C_4$alkoxy which is substituted by OH, or by phenyl, phenoxy or phenylcarbamoyl, the phenyl moiety in each of which may be substituted by $C_1$-$C_4$alkyl, $C_1$-$C_4$alkoxy or phenoxy, or R is $C_5$-$C_8$cycloalkyl which is unsubstituted or substituted by $C_1$-$C_4$alkyl, or R is a naphthyl or phenyl radical which is unsubstituted or substituted by $C_1$-$C_4$alkyl, $C_1$-$C_4$alkoxy, fluorine, chlorine, bromine, nitro, $C_1$-$C_4$alkylcarbonylamino or $C_1$-$C_4$alkoxycarbonyl, and
X is hydrogen or a halogen which is in 6- or 7-position.

2. A compound according to claim 1, wherein R is $C_1$-$C_6$alkyl which is unsubstituted or substituted by phenyl, phenoxy or phenylcarbamoyl, the phenyl moiety in each of which last three mentioned radicals may be substituted by $C_1$-$C_4$alkyl, $C_1$-$C_4$alkoxy or phenoxy, or is phenyl or phenyl which is substituted by $C_1$-$C_4$alkyl.

3. A compound according to claim 1, wherein X is hydrogen.

4. A process for the preparation of a compound of the formula

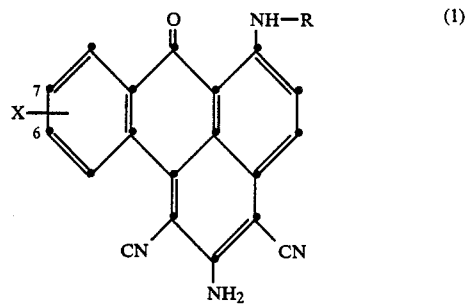

wherein
R is hydrogen or $C_1$-$C_8$alkyl which is unsubstituted or substituted by OH, $C_1$-$C_4$alkoxy or $C_1$-$C_4$alkoxy which is substituted by OH, or by phenyl, phenoxy or phenylcarbamoyl, the phenyl moiety in each of which may be substituted by $C_1$-$C_4$alkyl, $C_1$-$C_4$alkoxy or phenoxy, or R is $C_5$-$C_8$cycloalkyl which is unsubstituted or substituted by $C_1$-$C_4$alkyl, or R is a naphthyl or phenyl radical which is unsubstituted or substituted by $C_1$-$C_4$alkyl, $C_1$-$C_4$alkoxy, fluorine, chlorine, bromine, nitro, $C_1$-$C_4$alkylcarbonylamino or $C_1$-$C_4$alkoxycarbonyl and
X is hydrogen or a halogen which is in 6- or 7-position, which comprises reacting an aminoanthraquinone of formula

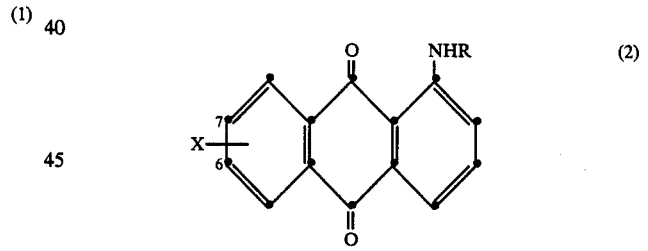

wherein X and R are as defined for formula (1), with malodinitrile in an inert solvent and in the presence of titanium tetrachloride and a tertiary amine.

5. A process according to claim 4, wherein the inert solvent is an aliphatic hydrocarbon, a chlorinated hydrocarbon, an ether or an aromatic compound.

6. A process according to claim 5, wherein the inert solvent is a chlorinated hydrocarbon.

7. A process according to claim 4, wherein the tertiary amine is an aliphatic or aromatic amine.

8. A process according to claim 7, wherein the tertiary amine is pyridine.

9. A process according to claim 4, wherein 2 moles to 3 moles of malodinitrile are used per mole of anthraquinone compound of formula (2).

10. A process according to claim 4, wherein 2 to 10 moles, of titanium tetrachloride are used per mole of anthraquinone compound of formula (2).

11. A process according to claim 4, wherein 2 to 6 moles of tertiary amine are used per mole of titanium tetrachloride.

12. A process according to claim 6, wherein the inert solvent is methylene chloride.

13. A process according to claim 9, wherein 2.2 to 3 moles of malodinitrile are used per mole of anthraquinone compound of formula (2).

14. A process according to claim 10, wherein 3 to 6 moles of titanium tetrachloride are used per mole of anthraquinone compound of formula (2).

* * * * *